(12) United States Patent
Ridell et al.

(10) Patent No.: US 10,947,705 B2
(45) Date of Patent: Mar. 16, 2021

(54) METHOD FOR RECYCLING WATER AND A WATER RECYCLING DEVICE

(71) Applicant: ORBITAL SYSTEMS AB, Malmö (SE)

(72) Inventors: Michael Ridell, Staffanstorp (SE); Richard Boden, Malmö (SE)

(73) Assignee: ORBITAL SYSTEMS AB, Malmö (SE)

( * ) Notice: Subject to any disclaimer, the term of this patent is extended or adjusted under 35 U.S.C. 154(b) by 0 days.

(21) Appl. No.: 16/462,860

(22) PCT Filed: Nov. 22, 2017

(86) PCT No.: PCT/SE2017/051159
§ 371 (c)(1),
(2) Date: May 21, 2019

(87) PCT Pub. No.: WO2018/097790
PCT Pub. Date: May 31, 2018

(65) Prior Publication Data
US 2019/0301145 A1    Oct. 3, 2019

(30) Foreign Application Priority Data

Nov. 25, 2016  (SE) .................................... 1651550-4
Nov. 25, 2016  (SE) .................................... 1651553-8

(51) Int. Cl.
*E03B 1/04*    (2006.01)
*A61L 2/10*    (2006.01)
(Continued)

(52) U.S. Cl.
CPC .................................... *E03B 1/04* (2013.01); *A61L 2/10* (2013.01); *A61L 2/26* (2013.01); *C02F 1/001* (2013.01);
(Continued)

(58) Field of Classification Search
None
See application file for complete search history.

(56) References Cited

U.S. PATENT DOCUMENTS 5,206,963 A    5/1993 Wiens
5,293,654 A    3/1994 Castwall et al.
(Continued)

FOREIGN PATENT DOCUMENTS

CN    105862992 A    8/1970
CN    101579198 A    11/2009
(Continued)

OTHER PUBLICATIONS

Swedish Search Report for patent application No. 1651550-4, dated Jun. 27, 2017.
(Continued)

*Primary Examiner* — Richard C Gurtowski
(74) *Attorney, Agent, or Firm* — Moser Taboada

(57) ABSTRACT

The present inventive concept relates to a method for recycling water in a water recycling device, the method comprising: receiving used water via a drain; determining a water quality measure of the used water; if the water; quality measure of the water is above a first quality threshold, feeding the used water to a valve arrangement; in the valve arrangement, forming water to be treated by providing external water, the used water or a combination of the external water and the used water; generating treated water by treating the water to be treated using a water treatment arrangement; and feeding the treated water to an outlet. The present inventive concept also relates to a water recycling device.

14 Claims, 10 Drawing Sheets

(51) Int. Cl.
*A61L 2/26* (2006.01)
*C02F 1/00* (2006.01)
*C02F 1/32* (2006.01)
*E03C 1/12* (2006.01)
*C02F 103/00* (2006.01)

(52) U.S. Cl.
CPC ............... *C02F 1/325* (2013.01); *E03C 1/12* (2013.01); *A61L 2202/11* (2013.01); *C02F 2103/002* (2013.01); *C02F 2201/005* (2013.01); *C02F 2303/04* (2013.01); *E03C 2201/40* (2013.01); *Y02A 20/148* (2018.01); *Y02A 20/30* (2018.01)

(56) References Cited

U.S. PATENT DOCUMENTS

| | | | |
|---|---|---|---|
| 2010/0043129 A1* | 2/2010 | Platteel | E03B 1/04 4/300 |
| 2011/0146800 A1 | 6/2011 | Jallon et al. | |
| 2011/0289672 A1 | 12/2011 | Cummings | |

FOREIGN PATENT DOCUMENTS

| | | |
|---|---|---|
| DE | 4239137 A1 | 5/1993 |
| EP | 2206838 A1 | 7/2010 |
| EP | 2818598 A1 | 12/2014 |
| SE | 469413 B | 5/1993 |
| WO | WO-2004101902 A1 | 11/2004 |
| WO | WO-2009147647 A1 | 12/2009 |
| WO | WO-2012061905 A1 | 5/2012 |
| WO | WO-2012146051 A1 | 11/2012 |
| WO | WO-2013095278 A1 | 6/2013 |
| WO | WO-2015094107 A1 | 6/2015 |
| WO | WO-2015094109 A1 | 6/2015 |
| WO | WO-2016177552 A1 | 11/2016 |

OTHER PUBLICATIONS

Swedish Search Report for patent application No. 1651553-8, dated Jun. 27, 2017.

* cited by examiner

1742

METHOD FOR RECYCLING WATER AND A WATER RECYCLING DEVICE

TECHNICAL FIELD

The apparatuses, systems and methods described herein generally relates to water recycling. More particularly, concepts for improved hygienic conditions in water recycling applications are being presented.

BACKGROUND

In many parts of the world, clean water is becoming a scarce commodity. Consequently, systems for purification and recycling of water has found applications across many fields. Conventional water recycling devices can be effective, but is often costly, and requires frequent maintenance and major modifications to existing piping.

An example of a water recycling device is known from e.g. SE469413. However, there is still a need for improved water recycling devices in terms of reliability of removal of contaminants, cost, and ease of installation.

SUMMARY OF THE INVENTION

It is an object of the present inventive concept to mitigate, alleviate or eliminate one or more of the above-identified deficiencies in the art and disadvantages singly or in combination.

According to a first aspect of the inventive concept, these and other objects are achieved in full, or at least in part, by a method for recycling water in a water recycling device, said method comprising: receiving used water via a drain; determining a water quality measure of said used water; if said water quality measure of said used water is above a first quality threshold, feeding said used water to a valve arrangement; in said valve arrangement, forming water to be treated by providing external water, said used water or a combination of said external water and said used water; generating treated water by treating said water to be treated using a water treatment arrangement; and feeding said treated water to an outlet.

The step of forming water to be treated by providing external water, said used water or a combination of said external water and said used water, may comprise sub-steps of providing only said external water for forming said water to be treated if said water quality measure is below said first quality threshold, or providing only said used water for forming said water to be treated if said water quality measure is above said first quality threshold The step of forming water to be treated by providing external water, said used water or a combination of said external water and said used water, may comprise sub-steps of providing only said external water for forming said water to be treated if said water quality measure is below said first quality threshold and a second quality threshold, providing said combination of said external water and said used water for forming said water to be treated if said water quality measure is above said first quality threshold but below said second quality threshold, or providing only said used water for forming said water to be treated if said water quality measure is above said first quality threshold and said second quality threshold.

The step of generating treated water by treating said water to be treated using a water treatment arrangement may comprise sub-steps of filtering said water to be treated, and reducing a harmful effect of microorganisms in said water to be treated by using UV light.

According to a second aspect of the inventive concept, these and other objects are achieved in full, or at least in part, by a water recycling device comprising: an outlet configured to output treated water; a drain for collecting used water output from said outlet; a return path in liquid communication with said drain; a treatment path in liquid communication with said return path and said outlet; a external water path in liquid communication with said treatment path, said external water path being connected to a external water outlet; a valve arrangement configured to accept as inputs said used water from said return path and/or external water from said external water path, said valve arrangement being placed between said return path and said treatment path, said valve arrangement being configured to direct said inputs to said treatment path, said valve arrangement being configured to mix said external water with said water from said return path; a circulation pump for providing a flow in said water recycling device; and a water treatment arrangement placed downstream of said valve arrangement.

The water recycling device may comprise a heating arrangement placed downstream of and/or combined with said water treatment arrangement.

The heating arrangement may be combined with a UV light treatment arrangement into a single piece of equipment The water treatment arrangement may comprise a filter arrangement.

The water recycling device may comprise a valve discard path configured to discharge water from said water recycling device, and said valve arrangement may be further configured to direct said water from said return path to said valve discard path.

The valve arrangement may comprise at least a first and a second valve arrangement, and said first valve may be configured to accept as input said used water from said return path, said first valve arrangement may be configured to direct said used water from said return path to said treatment path, and said second valve arrangement may accept as input said external water from said external water path, said second valve arrangement may be configured to direct said external water to said treatment path.

The first valve arrangement may be configured to direct said used water from said return path to said valve discard path The drain may comprise a drain discard path configured to discharge used water from said water recycling device.

The water recycling device may comprise a sensor arrangement configured to measure a water quality parameter in water in the water recycling device.

The sensor arrangement may comprise an electrical conductivity sensor and a UV-sensor.

The UV sensor may be arranged in said heating arrangement.

According to a third aspect of the inventive concept, these and other objects are achieved in full, or at least in part, by a water recirculating shower comprising a water recycling device according to the second aspect of the inventive concept.

Other objectives, features and advantages of the present inventive concept will appear from the following detailed disclosure, from the attached claims as well as from the drawings.

Generally, all terms used in the claims are to be interpreted according to their ordinary meaning in the technical field, unless explicitly defined otherwise herein. All references to "a/an/the [element, device, component, means, step, etc]" are to be interpreted openly as referring to at least one instance of said element, device, component, means, step, etc., unless explicitly stated otherwise. The steps of any method disclosed herein do not have to be performed in the exact order disclosed, unless explicitly stated.

BRIEF DESCRIPTION OF THE DRAWINGS

The above, as well as additional objects, features and advantages of the present inventive concept, will be better understood through the following illustrative and non-limiting detailed description of different embodiments of the present inventive concept, with reference to the appended drawings, wherein.

DETAILED DESCRIPTION

The present disclosure describes a water recycling device and methods related to the same. Initially, some terminology may be defined to provide clarification for the following disclosure.

In general, it has been realized by the inventors that hygienic conditions in a water recycling device can be improved by not allowing used water not adequate for recycling to contaminate external water in the water recycling device. Further, it has been realized that hygienic conditions in a water recycling device can be improved by allowing water from an external water source to pass a water treatment arrangement.

Throughout the present disclosure, reference is made to "external water". External water could be for example tap water or similar. The term "external water" may herein be used for water entering the water recycling device from an external water source. The quality of external water may vary between applications. Further, the quality of external water may vary between different countries.

Throughout the present disclosure, reference is made to "treated water" as well as "used water". Treated water may be water which has passed a water treatment arrangement and/or a heating arrangement. Treated water which leaves an outlet of the water recycling device may be referred to as used water.

Throughout the present disclosure, reference is made to different paths. Such paths may be for example pipes for transporting water.

Throughout the present disclosure, references are made to features being arranged "downstream" and/or "upstream" of certain features. The flow direction to which the terms "downstream" and "upstream" refer should be understood to be a flow direction from the drain to the outlet. In other words, the "stream" referred to in the terms "downstream" and "upstream" is a stream flowing from the drain to the outlet.

Throughout the present disclosure, reference is made to a "cleaning" of the water recycling device. In this context, cleaning may refer to a flushing of the water recycling device, and/or a flushing and a cleaning of the water recycling device with a cleaning agent.

It is to be understood that a water recycling device may refer to a water recirculation device.

Figure 1:
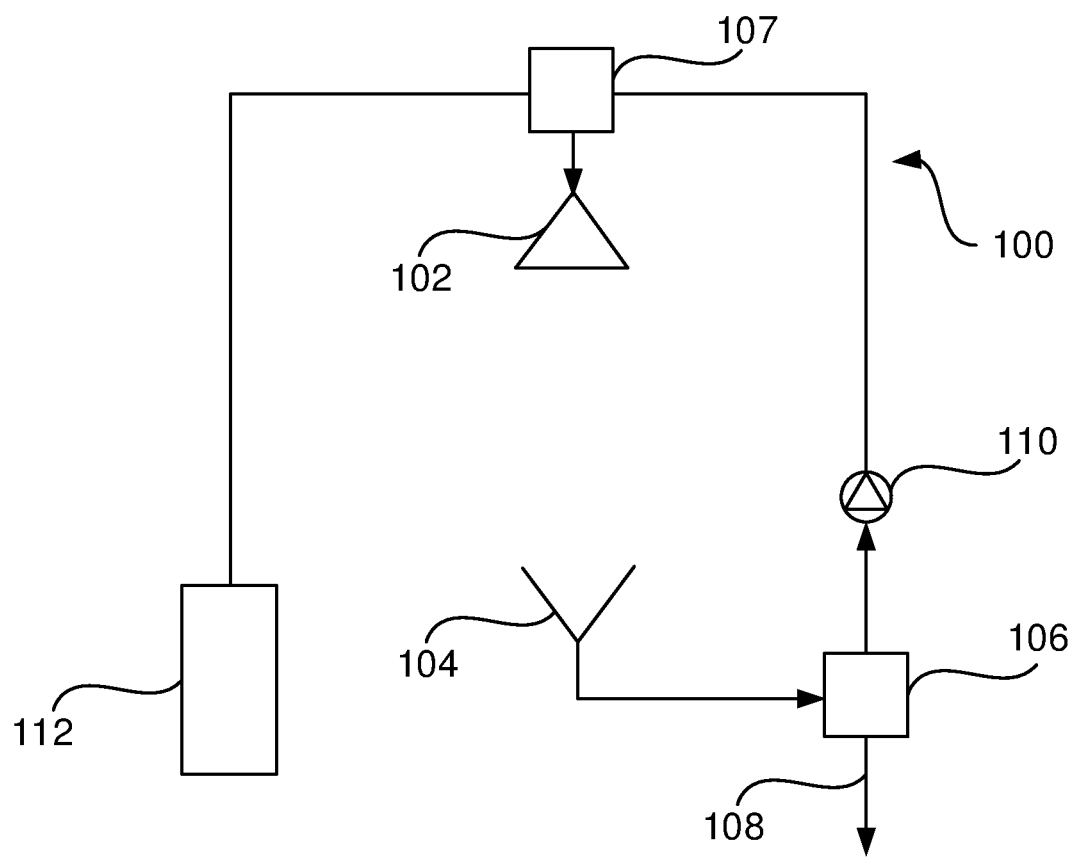
FIG. 1 schematically illustrates a conventional recirculation loop for recycling water in a shower.

With reference to FIG. 1, a conventional recirculation loop 100 for recycling water in a shower is shown. The recirculation loop 100 comprises a drain 104 for collecting water emitted from a nozzle 102. The water collected by the drain 104 is directed to a valve 106 which is configured to direct the water either to a discard water pipe 108 or towards the nozzle 102. A pump 110 provides a flow towards a valve 107, which accepts as inputs the collected water and potable water from a potable water source 112. The collected water can then be mixed with the potable water, and emitted through the nozzle 102. In some cases, the potable water may be exchanged for water being non-potable.

Figure 2:
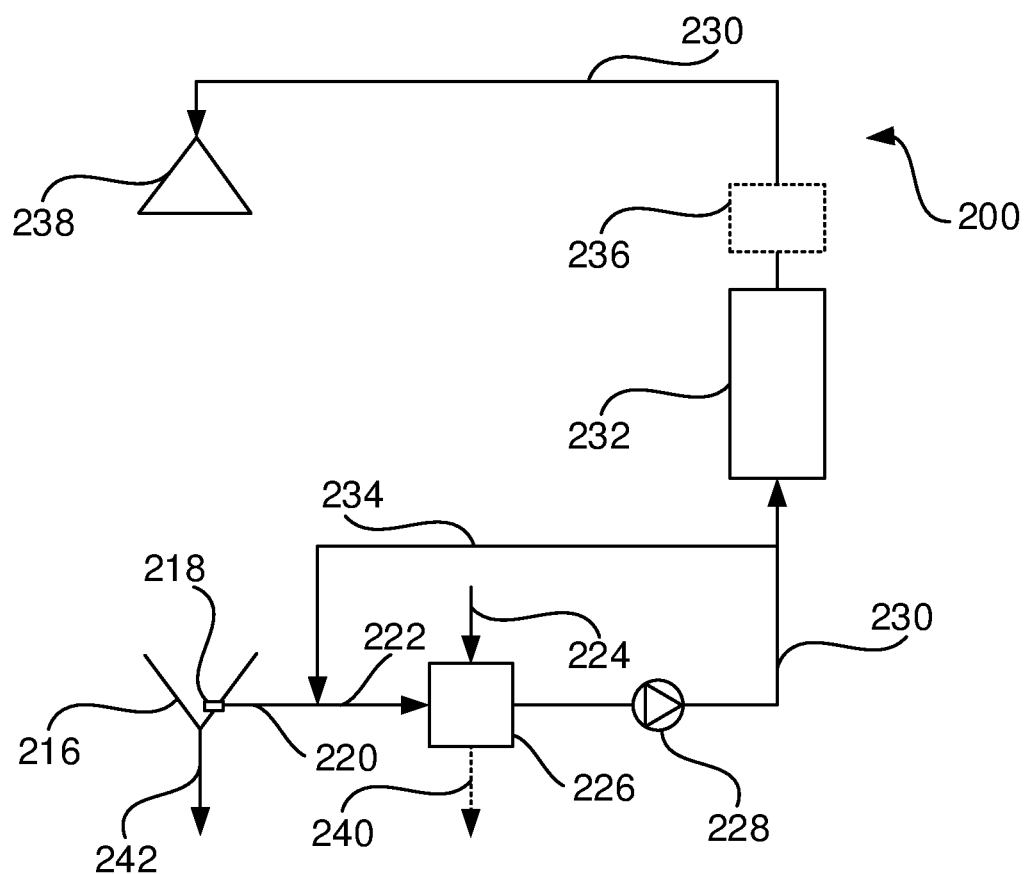
FIG. 2 schematically illustrates an example of a water recycling device.

With reference to FIG. 2, a water recycling device 200 is shown. The water recycling device 200 comprises an outlet 238 configured to output water. The outlet 238 may be a showerhead, a nozzle, or the like. The water recycling device further comprises a drain 216 for collecting the water output by the outlet, a return/evacuation path (R/E path) 220 in liquid communication with the drain 216, wherein the R/E path 220 comprises an inlet 218 for receiving water collected by the drain 216. Water collected by the drain 216 may hereafter be referred to as used water. The R/E path is in liquid communication with a return path 222. The return path 222 is in liquid communication with a treatment path 230. The treatment path is in liquid communication with the outlet 238. External water may enter the water recycling device via an external water path 224 in liquid communication with the treatment path 230, wherein the external water path 224 is connected to a external water source. Water in the treatment path 230 may hereafter be referred to as water to be treated. A valve arrangement 226 may be placed between the return path 222 and the treatment path 230. The valve arrangement 226 may be configured to accept as inputs water from the return path, for example used water, and/or external water from the external water path. The valve arrangement 226 may be configured to direct the inputs to the treatment path 230. The valve arrangement 226 may be configured to mix the external water with the water from the return path, for example the used water. The valve arrangement may comprise a valve discard path 240. The valve discard path may be configured to discharge water from the water recycling device 200. A circulation pump 228 may be placed downstream of the valve arrangement 226. The circulation pump 228 may provide for at least part of a flow of water in said water recycling device 200. A water treatment arrangement 232 may be placed downstream of the valve arrangement 226. The water treatment arrangement 232 may comprise a filter arrangement and/or a UV light treatment arrangement. The water treatment arrangement 232 may comprise at least one filter, such as a nanofilter, a microfilter, or a nanofilter and a microfilter. The water treatment arrangement 232 may comprise at least one particle filter and at least one microbiological filter. The water treatment arrangement 232 may comprise at least one active substance for reducing harmful effects of microorganisms in water passing the water treatment arrangement 232. Such an active substance may for example be contained within a filter media of the filter, and/or be released to the water inside the water treatment arrangement 232. Water which has been treated by the water treatment arrangement 232 may hereafter be referred to as treated water.

A heating arrangement 236 may be placed downstream of the water treatment arrangement 232. By first reducing harmful effects of microorganisms in water in the water recycling device 200 and subsequently heat the water in the water recycling device 200, the risk for microbiological growth is reduced compared to if the water, for example being a combination of used water and external water, is first heated and then treated, i.e. filtered and UV-light treated. A reason for this being the case is that the heating arrangement may for example heat the water to a temperature where microbiological growth is favorable. The heating arrangement 236 may heat water passing the heating arrangement 236. The heating arrangement 236 may comprise a UV light treatment arrangement. The heating arrangement 236 may be combined with the water treatment arrangement 232. The heating arrangement 236 may comprise a UV sensor configured to detect UV light emitted from the UV light treatment arrangement after the UV light has passed through water contained within the heating arrangement 236. The heating arrangement 236 may comprise a single piece of equipment for heating and UV light treating water. The heating arrangement 236 may provide a treatment of water. For example, the UV device may assist in reducing the harmful effects of microorganisms present in the water passing the heating arrangement 236. Thus, water which has passed the heating arrangement 236 may be referred to as treated water.

Still referring to FIG. 2, the water recycling device 200 may comprise an evacuation path 234 in liquid communication with the treatment path 230. An inlet of the evacuation path 234 may be placed downstream of the circulation pump. An inlet of the evacuation path 234 may be placed upstream of the water treatment arrangement 232. The evacuation path 234 may comprise an evacuation valve arrangement configured to regulate a flow of water from the treatment path into the evacuation path. The evacuation path 234 may be in liquid communication with the R/E path 220. The R/E path 220 may be configured to direct water received from the evacuation path 234, to the drain via the inlet of the R/E path 220.

The water recycling device 200 may be configured to heat water in the heating arrangement 236 and subsequently drain the heated water via the evacuation path to the R/E path 220.

The R/E path 220 may be configured to be in a first state, wherein water in the R/E path is allowed to flow in a direction away from the drain 216. The first state of the R/E path 220 may be achieved by not allowing water to flow through the evacuation path 234.

The R/E path 220 may be configured to be in a second state, wherein water in the R/E path is allowed to flow in a direction towards the drain 216. The second state of the R/E path 220 may be achieved by having the valve arrangement 226 set to accept only external water via the external water path 224 as input, by having the circulation pump 228 in operation, and by allowing water to flow through the evacuation path 234. Another example of achieving the second state of the R/E path 220 is by having the circulation pump 228 stopped, not accepting external water via the external water path 224 as input, and by allowing water to flow through the evacuation path 234.

Below, a number of advantages with the arrangement according to the present disclosure is presented. Reference will be made to used water, external water, and treated water. However, it is to be understood that these types of water may be interchangeable, and that any combination of external, used, and treated water is possible within the scope of the present disclosure.

An advantage with an arrangement according to the present disclosure is that a water quality measure of the used water collected by the drain 216 may be performed in the drain 216. Consequently, a decision may be made whether to recycle the used water, and thus direct the water via the inlet 218 to the water treatment arrangement 232, or if the used water should be discarded via the drain discard path 242. If the water is deemed to be inadequate for recycling, for example if a water quality measure of the used water is below a first quality threshold, the used water may be directed to the drain discard path 242. The used water thus never enters the return path 222 leading to the valve arrangement 226 where external water is input via the external water path 224. As a result, a risk of used water having a water quality measure below a first quality threshold contaminating the external water is reduced.

Another advantage with an arrangement according to the present disclosure is that external water input via the external water path 224 to the valve arrangement 226 may be treated in the water treatment arrangement 232 before being output by the outlet 238. Thus, a risk of allowing water containing contaminants to be output by the outlet 238 is reduced.

Yet another advantage with an arrangement according to the present disclosure is that water in at least part of the treatment path 230, such as water in a part of the treatment path 230 being upstream of the inlet of the evacuation path 234, and/or water in the water treatment arrangement 232, and/or water in the heating arrangement 236, may drain via the evacuation path 234, via the return path 222, and via the R/E path 220 to the drain 216. By doing this, water may be prevented from standing inside the water treatment arrangement 232. In other words, the water recycling device 200 may be emptied. In one example water may be heated in the heating arrangement 236 and subsequently drained, through the water treatment arrangement 232, via the evacuation path 234 and the R/E path 220 to the drain 216. This process may be repeated a number of times until a desired effect has been reached. Such a desired effect may for example be a reduction of contaminants in the water treatment arrangement 232. In this context, contaminants should be given a broad interpretation, meaning any kind of substance harmful to humans or to the functionality of the water recycling device. The process of draining water from the water recycle device may be automated and/or scheduled to be performed at specific intervals. Hereby, the water treatment arrangement 232, evacuation path 234, R/E path 220 and drain 216 may be flushed with heated water. Heated water may in some cases provide a more efficient flushing and/or cleaning compared to water which has not been heated. The water recycling device 200 may be arranged such that evacuation of the water recycling device 200 may be performed using gravity. For example, the water recycling device 200 may be arranged such that no water traps are formed in the different paths of the water recycling device 200. Further, the water recycling device 200 may be configured to be installed such that the heating arrangement 236 is arranged above the water treatment arrangement 232 with respect to gravity. Similarly, the evacuation path 234 may be arranged above the R/E path 220 with respect to gravity. In one example, the circulation pump 228, and/or another pump arranged in the water recycling device 200, may provide for a flow of water such that the water recycling device 200 can be emptied.

Yet another advantage with an arrangement according to the present disclosure is that external water may enter the valve arrangement 226, flow via the treatment path 230 to the inlet of the evacuation path 234, and be directed to the drain 216 via the return path 222 and R/E path 220. Hereby, the water recycling device 200 may be flushed with external water. For example, the drain 216 may be flushed by external water. The drain 216 may for example comprise a pre-filter for filtering water collected from the outlet 238, such as used water. The pre-filter may be a mesh filter. In this case yet another advantage is that the pre-filter may be flushed by external water. The water recycling device 200 may comprise a sensor arrangement. The sensor arrangement may be arranged in the drain 216. The sensor arrangement may be configured to measure a number of water quality parameters in water in the water recycling device and/or in water collected by the drain 216. The sensor arrangement may be configured to determine a water quality measure of water in the water recycling device. The sensor arrangement may comprise an electrical conductivity sensor and a UV-sensor. The electrical conductivity sensor may be arranged in the drain 216. The UV-sensor may be arranged in the heating arrangement 236. In this case yet another advantage is that external water may pass the sensor arrangement when the water recycling device is emptied, and thus external water may be measured by the sensor arrangement in order to set a reference value for the number of water quality parameter.

Yet another advantage with an arrangement according to the present disclosure is that water in at least part of the treatment path 230, the evacuation path 234, and return path 222 may circulate in the treatment path 230, the evacuation path 234, and return path 222. In other words, at least part of the treatment path 230, the evacuation path 234, and return path 222 may form a loop. This water may for example be used water, external water, treated water, or any combination of used, external, and treated water. Hereby, the circulation pump 228 may be flushed.

Yet another advantage with an arrangement according to the present disclosure is that an internal cleaning and disinfection may be achieved by adding chemicals to the drain 216 and a disinfection cycle may subsequently be triggered. The disinfection cycle may draw water, containing the chemicals, from the drain 216 into any of the water treatment arrangement 232, circulation pump 228, valve arrangement 226, and heating arrangement 236, or any of the R/E path 220, return path 222, evacuation path 234, and treatment path 230. The disinfection cycle may be triggered from an application on a smart device, such as a smart phone.

The drain 216 may comprise a drain discard path 242. The drain discard path 242 may be separated from the inlet of the R/E path 220, such that used water which is not intended to be treated by the water treatment arrangement 232, and thus not intended to be recycled, does not have to enter the inlet of the R/E path 220 in order to reach the drain discard path 242. Hereby, contaminated water may be prevented from contaminating any of the elements being arranged downstream of the inlet of the R/E path 220.

Figure 3:
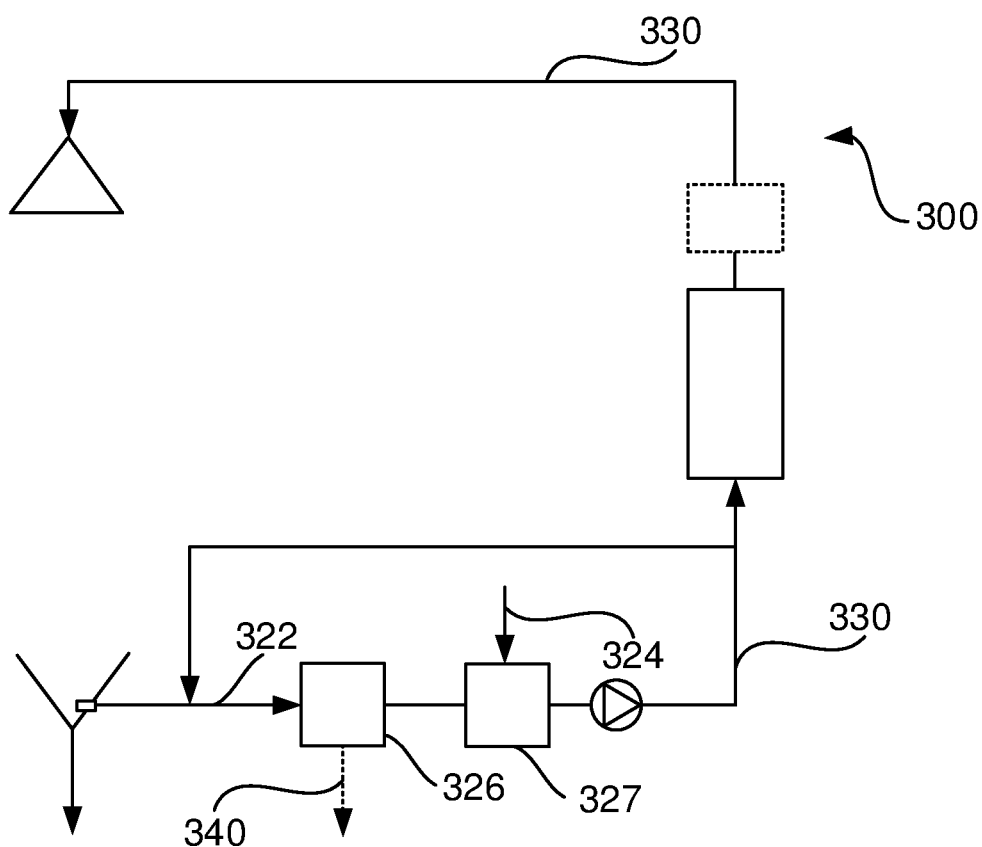
FIG. 3 schematically illustrates an example of a water recycling device.

Referring now to FIG. 3, a water recycling device 300 similar to the water recycling device 200 described in conjunction with FIG. 2 is illustrated. It is to be understood that the water recycling device 300 may comprise any of the features described above in conjunction with FIG. 2. The water recycling device 300 may comprise a first and a second valve arrangement 326, 327. The first valve arrangement 326 may be configured to accept as input the used water from the return path 322. The first valve arrangement may be configured to direct the used water from the return path 322 to the treatment path 330. The second valve arrangement 327 may accept as input the external water from the external water path 324. The second valve arrangement 327 may be configured to direct the external water to the treatment path 330. The second valve arrangement 327 may be configured to direct the used water received from the first valve arrangement 326 to the treatment path 330. The first valve arrangement 326 may be configured to direct the used water from the return path 322 to the valve discard path 340.

Figure 4:
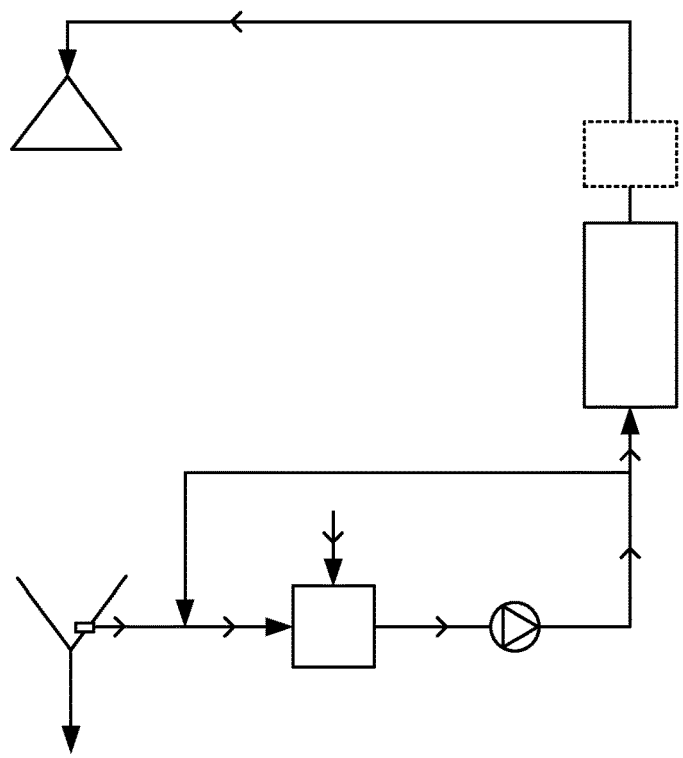
FIGS. 4-6 schematically illustrates flow directions in a water recycling device.
Figure 5:
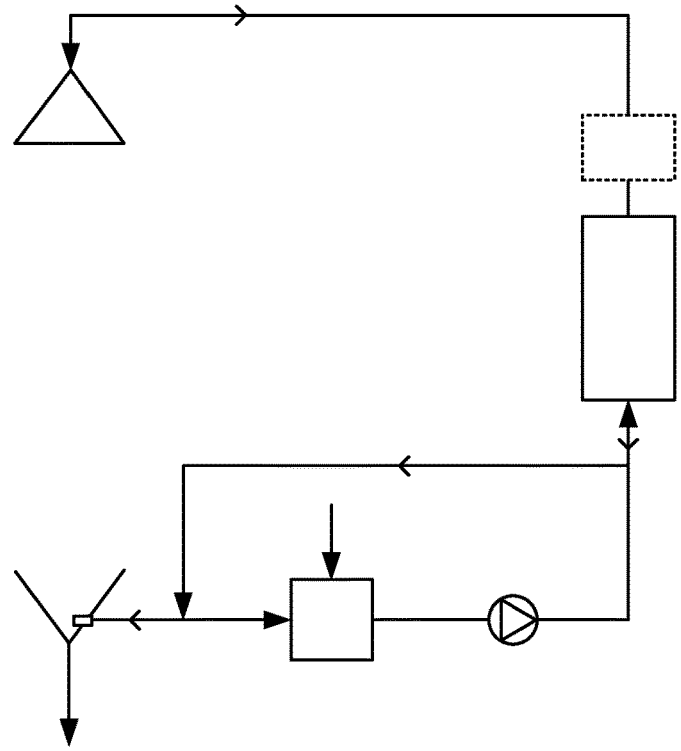
Figure 6:
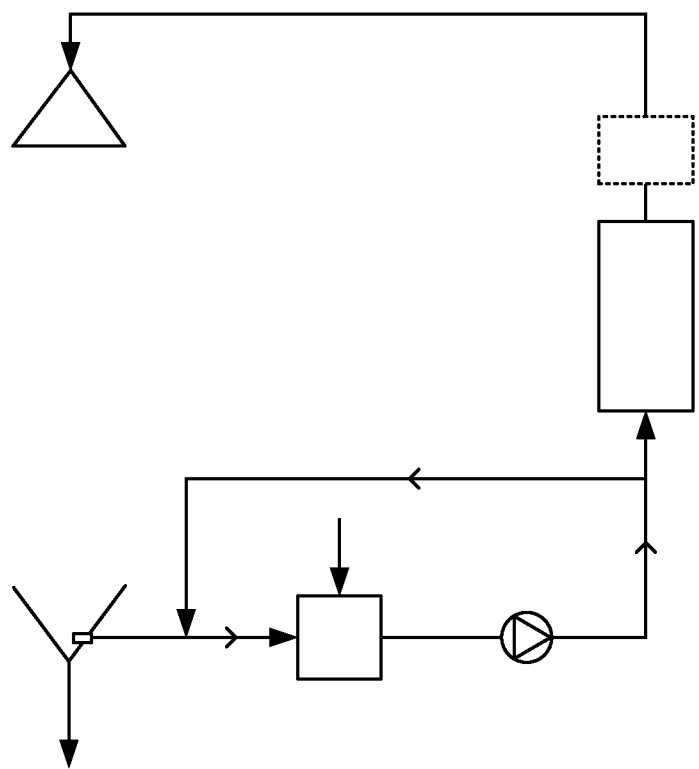

Referring now to FIGS. 4-6, flow directions in a water recycling device are illustrated. Referring first to FIG. 4, when outputting water from the water recycling device, used water may be collected by the drain and enter the R/E path via the inlet of the R/E path. The used water may then be directed to the return path, and the valve arrangement. Used water, and only used water, may thus be directed to the water treatment arrangement and output by the outlet of the water recycling device. This may for example be the case if a water quality measure of the used water is above a first quality threshold and a second quality threshold. At the valve arrangement, external water may enter the water recycling device. This may for example be the case if a water quality measure of the used water is above the first quality threshold, but below a second quality threshold. In other words, a combination of used water and external water is used. It is to be understood that it is possible to use only used water, only external water, or a combination of the two. External water, and only external water, may for example be used if a water quality measure of the used water below a first quality threshold. Water to be treated may then enter the treatment path via the circulation pump and be directed to the water treatment arrangement. Treated water may then enter the heating arrangement, and subsequently be output from the outlet.

It is also possible to direct used water to the evacuation path (not shown). In this case, used water in the treatment path is first allowed to leave the treatment path via the evacuation path, the R/E path, and the drain, and optionally via the outlet in case any used water has already passed the inlet of the evacuation path. External water may then enter the valve arrangement and subsequently enter the treatment path and be output from the outlet via the water treatment arrangement. Hereby, it is possible to discharge used water which is for any reason deemed to be inadequate for recycling, for example if a water quality measure of the used water is below a first quality threshold.

Yet another possibility is for used water to enter the drain, and subsequently enter the drain discard pipe. This may for example be the case if the used water is for any reason deemed to be inadequate for recycling, for example if a water quality measure of the used water is below the first quality threshold and the second quality threshold. In this case used water never enters the inlet of the R/E path. Instead, external water may enter the valve arrangement, and subsequently enter the treatment path and be output from the outlet via the water treatment arrangement.

Yet another possibility is to fill the water recycling device with water. For example, external water may be introduced to the water recycling device. This may be achieved by setting the valve arrangement to accept external water as input, the evacuation valve arrangement to prevent a flow of water into the evacuation path, and by the circulation pump providing a flow of water in the water recycling device.

External water may be allowed to fill the water recycling device to a level such that external water is introduced into the heating arrangement.

Referring now to FIG. 5, the evacuation valve arrangement may be set to allow a flow of water into the evacuation path, such that the water recycling device may be emptied. The circulation pump may in this case be turned off. Water may thus drain from the treatment path via the heating arrangement, the water treatment arrangement, the evacuation path, and the R/E path to the drain and subsequently to the drain discard pipe. When evacuating the water recycling device, air may be drawn through the outlet in order to equalize a pressure inside the water recycling device. The air drawn through the outlet may assist in keeping the water treatment arrangement dry, thus reducing the possibility of growth of microorganisms in the water treatment arrangement.

Referring now to FIG. 6, used water and/or external water may be looped through the treatment path, the evacuation path, and the return path. This may be achieved by first providing used and/or external water to the water recycling device. Subsequently, the valve arrangement may be set to only accept water received from the return path. The evacuation valve arrangement may be set to allow a flow of water into the evacuation path. The circulation pump may provide a flow for looping water through the treatment path, the evacuation path, and the return path.

Figure 7:
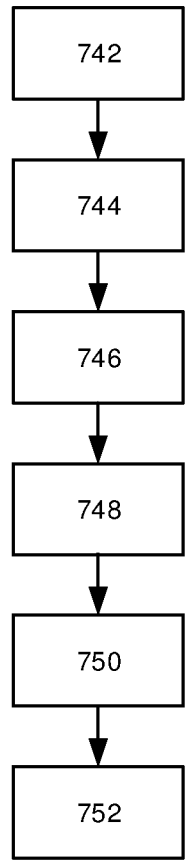
FIG. 7 is a flow chart diagram of a method for recycling water in a water recycling device.

Referring now to FIG. 7, a method for recycling water in a water recycling device is illustrated in a flow chart diagram. The method comprises the step 742 of receiving used water via a drain; the step 744 of determining a water quality measure of the used water; the step 746, if the water quality measure of the used water is above a first quality threshold, feeding the used water to a valve arrangement; the step 748 of, in said valve arrangement, forming water to be treated by providing external water, the used water or a combination of the external water and the used water; the step 750 of generating treated water by treating the water to be treated using a water treatment arrangement; and the step 752 of feeding the treated water to an outlet.

A method for recycling water in a water recycling device is described below. The water recycling device may comprise an outlet configured to output treated water; a drain for collecting used water output from said outlet; a return path in liquid communication with said drain; a treatment path in liquid communication with said return path and said outlet; an external water path in liquid communication with said treatment path, said external water path being connected to an external water outlet; a valve arrangement configured to accept as inputs said used water from said return path and/or external water from said external water path, said valve arrangement being placed between said return path and said treatment path, said valve arrangement being configured to direct said inputs to said treatment path, said valve arrangement being configured to mix said external water with said water from said return path; a circulation pump for providing a flow in said water recycling device; and a water treatment arrangement placed downstream of said valve arrangement. The method may comprise receiving used water via a drain; determining a water quality measure of the used water; if said water quality measure of the used water is above a first quality threshold, feeding the used water to a valve arrangement; in the valve arrangement, forming water to be treated by providing external water, the used water or a combination of the external water and the used water; generating treated water by treating the water to be treated using a water treatment arrangement; and feeding the treated water to an outlet.

The step of forming water to be treated by providing external water, the used water or a combination of the external water and the used water, may further comprise sub-steps of providing only the external water for forming the water to be treated if the water quality measure is below the first quality threshold and a second quality threshold; providing the combination of the external water and the used water for forming the water to be treated if the water quality measure is above the first quality threshold but below the second quality threshold; or providing only the used water for forming the water to be treated if the water quality measure is above the first quality threshold and the second quality threshold.

The step of generating treated water by treating the water to be treated using a water treatment arrangement may further comprise sub-steps of filtering the water to be treated; and reducing a harmful effect of microorganisms in the water to be treated by using UV light.

The water quality measure may for example be a measure of electrical conductivity in the used water. The water quality measure may be detected in used water in the drain of the water recycling device.

The inventive concept has mainly been described above with reference to a few embodiments. However, as is readily appreciated by a person skilled in the art, other embodiments than the ones disclosed above are equally possible within the scope of the inventive concept, as defined by the appended patent claims.

LIST OF REFERENCE SIGNS

100 Recirculation loop
102 Nozzle
104 Drain
106 Valve
107 Valve
108 Discard water pipe
110 Pump
112 Potable water source
200 Water recycling device
216 Drain
218 Inlet
220 Return/Evacuation path
222 Return path
224 External water path
226 Valve arrangement
228 Circulation pump
230 Treatment path
232 Water treatment arrangement
234 Evacuation path
236 Heating arrangement
238 Outlet
240 Valve discard path
242 Drain discard path
300 Water recycling device
322 Return path
324 External water path
326 First valve arrangement
327 Second valve arrangement
330 Treatment path
340 Valve discard path
742 Step of receiving used water
744 Step of determining a water quality measure
746 Step of feeding used water to a valve arrangement

748 Step of forming water to be treated
750 Step of generating treated water
752 Step of feeding treated water to an outlet The disclosure made in the following paragraphs relates to a related aspect of the inventive concept presented above. The apparatuses, systems and methods described below generally relates to water recycling. More particularly, concepts for improved hygienic conditions in water recycling applications are being presented.

In many parts of the world, clean water is becoming a scarce commodity. Consequently, systems for purification and recycling of water has found applications across many fields. Conventional water recycling devices can be effective, but is often costly, and requires frequent maintenance and major modifications to existing piping.

An example of a water recycling device is known from e.g. SE469413. However, there is still a need for improved water recycling devices in terms of reliability of removal of contaminants, cost, and ease of installation.

It is an object of the present inventive concept to mitigate, alleviate or eliminate one or more of the above-identified deficiencies in the art and disadvantages singly or in combination.

According to a fourth aspect of the inventive concept, these and other objects are achieved in full, or at least in part, by a water recycling device comprising: an outlet configured to output treated water; a drain for collecting used water output from the outlet; a return/evacuation path in liquid communication with the drain, wherein the return/evacuation path comprises an inlet for receiving water collected by the drain; a return path in liquid communication with the return/evacuation path; a treatment path in liquid communication with the return path and the outlet; an external water path in liquid communication with the treatment path, the external water path being connected to an external water outlet; a valve arrangement configured to accept as inputs used water from the return path and/or external water from the external water path, the valve arrangement being placed between the return path and the treatment path, the valve arrangement being configured to direct the inputs to the treatment path, the valve arrangement being configured to mix the external water with the used water from the return path; a circulation pump for providing a flow in the water recycling device; and a water treatment arrangement placed downstream of the valve arrangement.

The water recycling device may comprise a heating arrangement placed downstream of the water treatment arrangement.

The water recycling device may comprise an evacuation path in liquid communication with the treatment path, wherein the evacuation path is placed downstream of the valve arrangement and upstream of the water treatment arrangement.

The evacuation path may comprise an evacuation valve arrangement configured to regulate a flow of water from the treatment path into the evacuation path.

The evacuation path may be in liquid communication with the return/evacuation path.

The water recycling device may be configured to heat water in the heating arrangement and subsequently drain the heated water via the evacuation path to the return/evacuation path.

The water recycling device may be configured to circulate water in at least part of the treatment path, the evacuation path, and the return path.

The return/evacuation path may be configured to direct water received from the evacuation path to the drain via the inlet of the return/evacuation path.

The drain may comprise a drain discard path configured to discharge water from the water recycling device.

The return/evacuation path may be configured to be in a first state, wherein water in the return/evacuation path is allowed to flow in a direction away from the drain, and a second state, wherein water in the return/evacuation path is allowed to flow in a direction towards the drain.

The water recycling device may comprise a sensor arrangement configured to measure a water quality parameter in water in the water recycling device.

The sensor arrangement may comprise an electrical conductivity sensor and a UV-sensor.

According to a fifth aspect of the inventive concept, these and other objects are achieved in full, or at least in part, by a water recirculating shower comprising a water recycling device according to the first aspect of the inventive concept.

According to a sixth aspect of the inventive concept, these and other objects are achieved in full, or at least in part, by a method for evacuating a water recycling device, the water recycling device comprising: an outlet configured to output treated water; a drain for collecting used water output from the outlet; a return/evacuation path in liquid communication with the drain, wherein the return/evacuation path comprises an inlet for receiving water collected by the drain; a return path in liquid communication with the return/evacuation path; a treatment path in liquid communication with the return path and the outlet; an external water path in liquid communication with the treatment path, the external water path being connected to an external water outlet; a valve arrangement, wherein the valve arrangement is configured to accept as inputs used water from the return path and/or external water from the external water path, the valve arrangement being placed between the return path and the treatment path, the valve arrangement being configured to direct the inputs to the treatment path, the valve arrangement being configured to mix the external water with the used water from the return path; a circulation pump for providing a flow in the water recycling device; a water treatment arrangement placed downstream of the valve arrangement; and an evacuation path in liquid communication with the treatment path, wherein the evacuation path is placed downstream of the circulation pump and upstream of the water treatment arrangement; wherein the method comprises the steps of: feeding water in the water recycling device to the drain via the evacuation path and/or the return/evacuation path.

The step of feeding water in the water recycling device to the drain via the evacuation path and/or the return/evacuation path may be accomplished by gravity.

According to a seventh aspect of the inventive concept, these and other objects are achieved in full, or at least in part, by a method for cleaning a water recycling device, the water recycling device comprising: an outlet configured to output treated water; a drain for collecting used the water output from the outlet; a return/evacuation path in liquid communication with the drain, wherein the return/evacuation path comprises an inlet for receiving water collected by the drain; a return path in liquid communication with the return/evacuation path; a treatment path in liquid communication with the return path and the outlet; an external water path in liquid communication with the treatment path, the external water path being connected to an external water outlet; a valve arrangement, wherein the valve arrangement is configured to accept as inputs used water from the return path and/or external water from the external water path, the valve arrangement being placed between the return path and the treatment path, the valve arrangement being configured to direct the inputs to the treatment path, the valve arrangement being configured to mix the external water with the used water from the return path; a circulation pump for providing a flow in the water recycling device; a water treatment arrangement placed downstream of the valve arrangement; and an evacuation path in liquid communication with the treatment path, wherein the evacuation path is placed downstream of the circulation pump and upstream of the water treatment arrangement; the method comprising the steps of: providing the water recycling device with the used water, the external water, or a combination of the used water and the external water; and evacuating the water recycling device according to the second aspect of the inventive concept.

The step of providing the water recycling device with the used water, the external water, or the combination of the used water and the external water may comprise a sub-step of at least partly filling the water treatment arrangement with the used water, the external water, or a combination of the used water and the external water.

The step of providing the water recycling device with the used water, the external water, or the combination of the used water and the external water may comprise a sub-step of circulating the used water, the external water, or the combination of the used water and the external water in the evacuation path, the return path, and at least part of the treatment path.

The water recycling device may comprise a heater arrangement placed downstream of the water treatment arrangement and/or combined with the water treatment arrangement, and the step of providing the water recycling device with the used water, the external water, or the combination of the used water and the external water may comprise a sub-step of heating the used water, the external water, or the combination of the used water and the external water in the heating arrangement.

Other objectives, features and advantages of the present inventive concept will appear from the following detailed disclosure, from the attached clauses as well as from the drawings.

Generally, all terms used in the clauses are to be interpreted according to their ordinary meaning in the technical field, unless explicitly defined otherwise herein. All references to "a/an/the [element, device, component, means, step, etc]" are to be interpreted openly as referring to at least one instance of said element, device, component, means, step, etc., unless explicitly stated otherwise. The steps of any method disclosed herein do not have to be performed in the exact order disclosed, unless explicitly stated.

Figure 8:
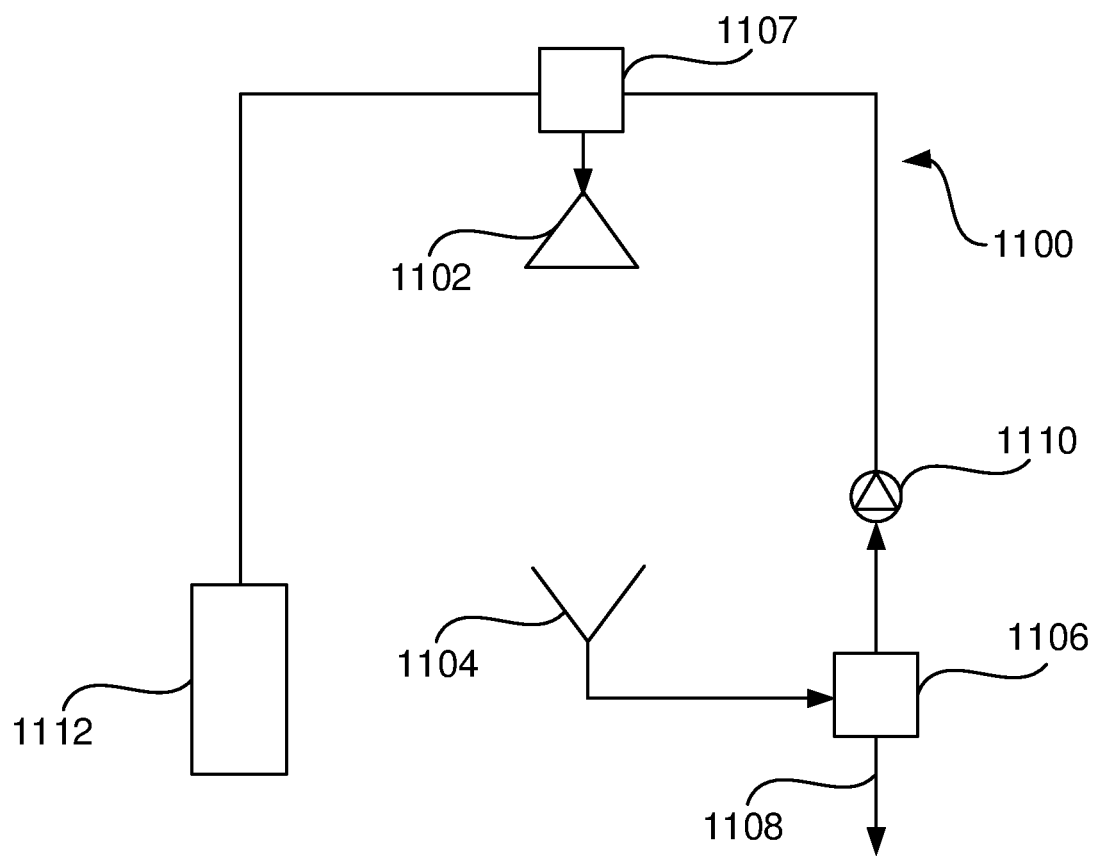
FIG. 8 schematically illustrates a conventional recirculation loop for recycling water in a shower.
Figure 9:
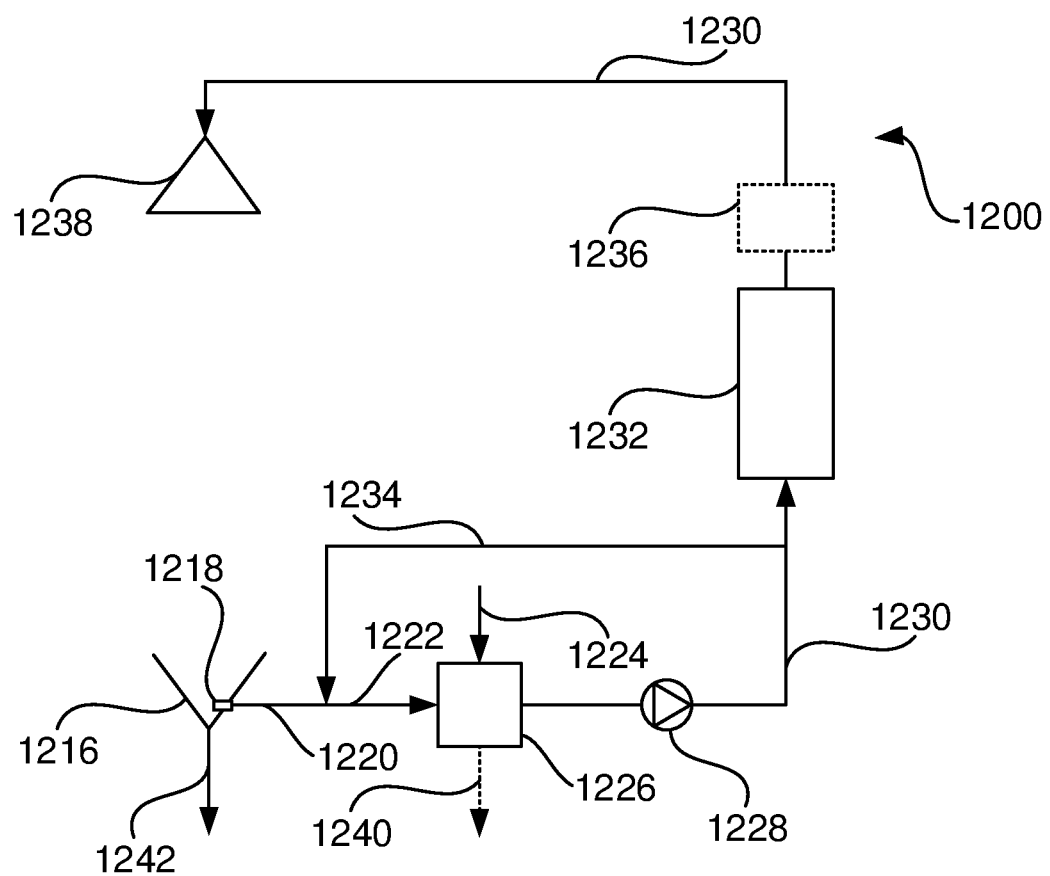
FIG. 9 schematically illustrates an example of a water recycling device.
Figure 10:
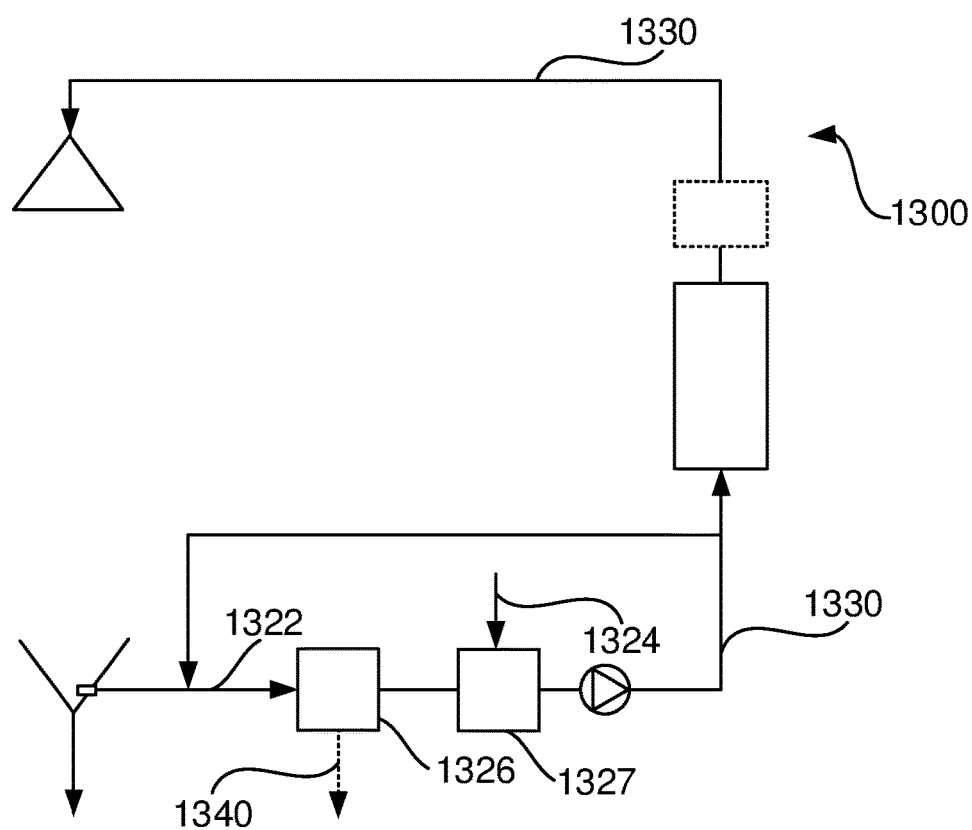
FIG. 10 schematically illustrates an example of a water recycling device.
Figure 11:
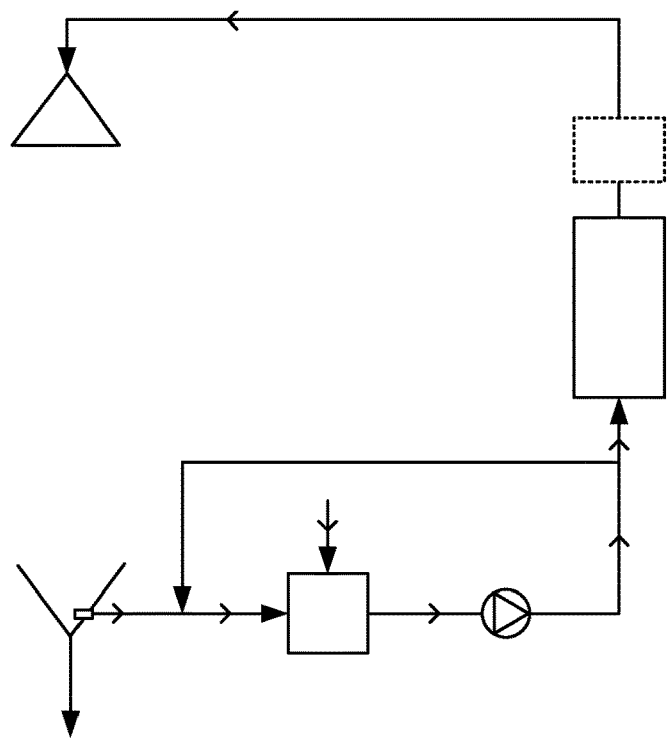
FIGS. 11-13 schematically illustrates flow directions in a water recycling device.
Figure 12:
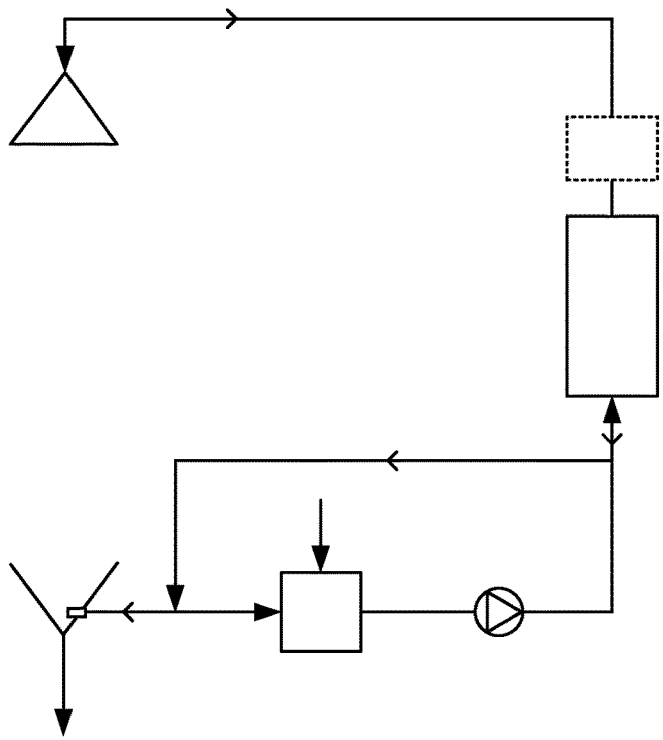
Figures 13, 14:
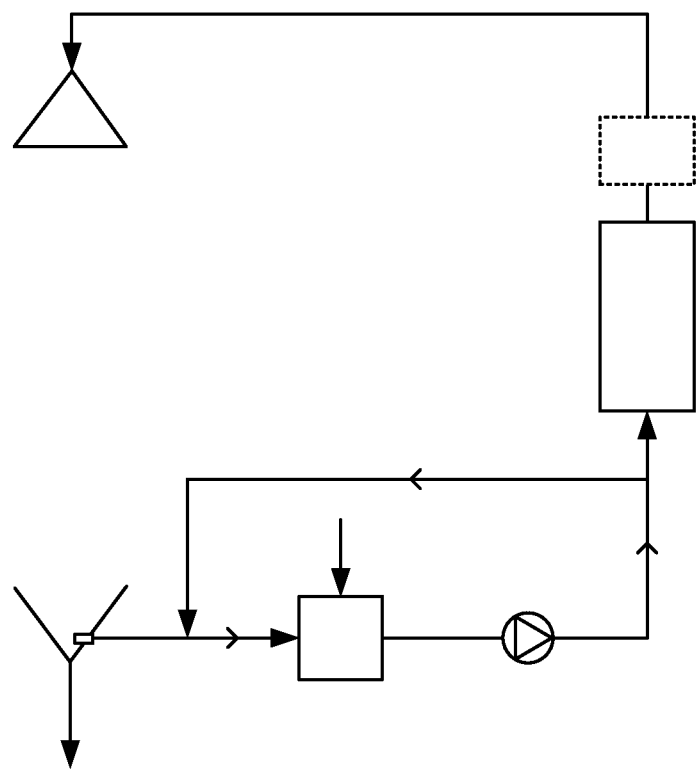
FIG. 14 is a flow chart diagram of a method for evacuating a water recycling device.

The above, as well as additional objects, features and advantages of the present inventive concept, will be better understood through the following illustrative and non-limiting detailed description of different embodiments of the present inventive concept, with reference to the appended drawings, wherein:

FIG. 8 schematically illustrates a conventional recirculation loop for recycling water in a shower;

FIG. 9 schematically illustrates an example of a water recycling device;

FIG. 10 schematically illustrates an example of a water recycling device;

FIGS. 11-13 schematically illustrates flow directions in a water recycling device.

FIG. 14 is a flow chart diagram of a method for evacuating a water recycling device.

The present disclosure describes a water recycling device and methods related to the same. Initially, some terminology may be defined to provide clarification for the following disclosure.

In general, it has been realized by the inventors that hygienic conditions in a water recycling device can be improved by draining water from the water recycling device when it is not used for recycling water, such as between uses, or at certain time intervals. By doing this, water may be prevented from becoming stagnant. It has further been realized that external water and/or water collected in a drain of the water recycling device may be used to flush the water recycling device.

Throughout the present disclosure, reference is made to "external water". External water could be for example tap water or similar. The term "external water" may herein be used for water entering the water recycling device from an external water source. The quality of external water may vary between applications. Further, the quality of external water may vary between different countries.

Throughout the present disclosure, reference is made to "treated water" as well as "used water". Treated water may be water which has passed a water treatment arrangement and/or a heating arrangement. Treated water which leaves an outlet of the water recycling device may be referred to as used water.

Throughout the present disclosure, reference is made to different paths. Such paths may be for example pipes for transporting water.

Throughout the present disclosure, references are made to features being arranged "downstream" and/or "upstream" of certain features. The flow direction to which the terms "downstream" and "upstream" refer should be understood to be a flow direction from the drain to the outlet. In other words, the "stream" referred to in the terms "downstream" and "upstream" is a stream flowing from the drain to the outlet.

Throughout the present disclosure, reference is made to a "cleaning" of the water recycling device. In this context, cleaning may refer to a flushing of the water recycling device, and/or a flushing and a cleaning of the water recycling device with a cleaning agent.

Throughout the present disclosure, a "water quality parameter" may be interchangeably used with a "water quality measure".

It is to be understood that a water recycling device may refer to a water recirculation device.

With reference to FIG. 8, a conventional recirculation loop 1100 for recycling water in a shower is shown. The recirculation loop 1100 comprises a drain 1104 for collecting water emitted from a nozzle 1102. The water collected by the drain 1104 is directed to a valve 1106 which is configured to direct the water either to a discard water pipe 1108 or towards the nozzle 1102. A pump 1110 provides a flow towards a valve 1107, which accepts as inputs the collected water and potable water from a potable water source 1112. The collected water can then be mixed with the potable water, and emitted through the nozzle 1102. In some cases, the potable water may be exchanged for water being non-potable.

With reference to FIG. 9, a water recycling device 1200 is shown. The water recycling device 1200 comprises an outlet 1238 configured to output water. The outlet 1238 may be a showerhead, a nozzle, or the like. The water recycling device further comprises a drain 1216 for collecting the water output by the outlet, a return/evacuation path (R/E path) 1220 in liquid communication with the drain 1216, wherein the R/E path 1220 comprises an inlet 1218 for receiving water collected by the drain 1216. Water collected by the drain 1216 may hereafter be referred to as used water. The R/E path is in liquid communication with a return path1 222. The return path 1222 is in liquid communication with a treatment path 1230. The treatment path is in liquid communication with the outlet 1238. External water may enter the water recycling device via an external water path 1224 in liquid communication with the treatment path 1230, wherein the external water path 1224 is connected to an external water source. Water in the treatment path 1230 may hereafter be referred to as water to be treated. A valve arrangement 1226 may be placed between the return path 1222 and the treatment path 1230. The valve arrangement 1226 may be configured to accept as inputs water from the return path, for example used water, and/or external water from the external water path. The valve arrangement 1226 may be configured to direct the inputs to the treatment path 1230. The valve arrangement 1226 may be configured to mix the external water with the water from the return path, for example the used water. The valve arrangement may comprise a valve discard path 1240. The valve discard path may be configured to discharge water from the water recycling device 1200. A circulation pump 1228 may be placed downstream of the valve arrangement 1226. The circulation pump 1228 may provide for at least part of a flow of water in said water recycling device 1200. A water treatment arrangement 1232 may be placed downstream of the valve arrangement 1226. The water treatment arrangement 1232 may comprise a filter arrangement and/or a UV light treatment arrangement. The water treatment arrangement 1232 may comprise at least one filter, such as a nanofilter, a microfilter, or a nanofilter and a microfilter. The water treatment arrangement 1232 may comprise at least one particle filter and at least one microbiological filter. The water treatment arrangement 1232 may comprise at least one active substance for reducing harmful effects of microorganisms in water passing the water treatment arrangement 1232. Such an active substance may for example be contained within a filter media of the filter, and/or be released to the water inside the water treatment arrangement 1232. Water which has been treated by the water treatment arrangement 1232 may hereafter be referred to as treated water.

A heating arrangement 1236 may be placed downstream of the water treatment arrangement 1232. By first reducing harmful effects of microorganisms in water in the water recycling device 1200 and subsequently heat the water in the water recycling device 1200, the risk for microbiological growth is reduced compared to if the water, for example being a combination of used water and external water, is first heated and then treated, i.e. filtered and UV-light treated. A reason for this being the case is that the heating arrangement may for example heat the water to a temperature where microbiological growth is favorable. The heating arrangement 1236 may heat water passing the heating arrangement 1236. The heating arrangement 1236 may comprise a UV light treatment arrangement. The heating arrangement 1236 may be combined with the water treatment arrangement 1232. The heating arrangement 1236 may comprise a UV sensor configured to detect UV light emitted from the UV light treatment arrangement after the UV light has passed through water contained within the heating arrangement 1236. The heating arrangement 1236 may comprise a single piece of equipment for heating and UV light treating water. The heating arrangement 1236 may provide a treatment of water. For example, the UV device may assist in reducing the harmful effects of microorganisms present in the water passing the heating arrangement 1236. Thus, water which has passed the heating arrangement 1236 may be referred to as treated water.

Still referring to FIG. 9, the water recycling device 1200 may comprise an evacuation path 1234 in liquid communication with the treatment path 1230. An inlet of the evacuation path 1234 may be placed downstream of the circulation pump. An inlet of the evacuation path 1234 may be placed upstream of the water treatment arrangement 1232. The evacuation path 1234 may comprise an evacuation valve arrangement configured to regulate a flow of water from the treatment path into the evacuation path. The evacuation path 1234 may be in liquid communication with the R/E path 1220. The R/E path 1220 may be configured to direct water received from the evacuation path 1234, to the drain via the inlet of the R/E path 1220.

The water recycling device 1200 may be configured to heat water in the heating arrangement 1236 and subsequently drain the heated water via the evacuation path to the R/E path 1220.

The R/E path 1220 may be configured to be in a first state, wherein water in the R/E path is allowed to flow in a direction away from the drain 1216. The first state of the R/E path 1220 may be achieved by not allowing water to flow through the evacuation path 1234.

The R/E path 1220 may be configured to be in a second state, wherein water in the R/E path is allowed to flow in a direction towards the drain 1216. The second state of the R/E path 1220 may be achieved by having the valve arrangement 1226 set to accept only external water via the external water path 1224 as input, by having the circulation pump 1228 in operation, and by allowing water to flow through the evacuation path 1234. Another example of achieving the second state of the R/E path 1220 is by having the circulation pump 1228 stopped, not accepting external water via the external water path 1224 as input, and by allowing water to flow through the evacuation path 1234.

Below, a number of advantages with the arrangement according to the present disclosure is presented. Reference will be made to used water, external water, and treated water. However, it is to be understood that these types of water may be interchangeable, and that any combination of external, used, and treated water is possible within the scope of the present disclosure.

An advantage with an arrangement according to the present disclosure is that a water quality measure of the used water collected by the drain 1216 may be performed in the drain 1216. Consequently, a decision may be made whether to recycle the used water, and thus direct the water via the inlet 1218 to the water treatment arrangement 1232, or if the used water should be discarded via the drain discard path 1242. If the water is deemed to be inadequate for recycling, for example if a water quality measure of the used water is below a first quality threshold, the used water may be directed to the drain discard path 1242. The used water thus never enters the return path 1222 leading to the valve arrangement 1226 where external water is input via the external water path 1224. As a result, a risk of used water having a water quality measure below a first quality threshold contaminating the external water is reduced. The water quality measure may for example be a measure of electrical conductivity in the used water. The water quality measure may be detected in used water in the drain of the water recycling device.

Another advantage with an arrangement according to the present disclosure is that external water input via the external water path 1224 to the valve arrangement 1226 may be treated in the water treatment arrangement 1232 before being output by the outlet 1238. Thus, a risk of allowing water containing contaminants to be output by the outlet 1238 is reduced.

Yet another advantage with an arrangement according to the present disclosure is that water in at least part of the treatment path 1230, such as water in a part of the treatment path 1230 being upstream of the inlet of the evacuation path 1234, and/or water in the water treatment arrangement 1232, and/or water in the heating arrangement 1236, may drain via the evacuation path 1234, via the return path 1222, and via the R/E path 1220 to the drain 1216. By doing this, water may be prevented from standing inside the water treatment arrangement 1232. In other words, the water recycling device 1200 may be emptied. In one example water may be heated in the heating arrangement 1236 and subsequently drained, through the water treatment arrangement 1232, via the evacuation path 1234 and the R/E path 1220 to the drain 1216. This process may be repeated a number of times until a desired effect has been reached. Such a desired effect may for example be a reduction of contaminants in the water treatment arrangement 1232. In this context, contaminants should be given a broad interpretation, meaning any kind of substance harmful to humans or to the functionality of the water recycling device. The process of draining water from the water recycle device may be automated and/or scheduled to be performed at specific intervals. Hereby, the water treatment arrangement 1232, evacuation path 1234, R/E path 1220 and drain 1216 may be flushed with heated water. Heated water may in some cases provide a more efficient flushing and/or cleaning compared to water which has not been heated. The water recycling device 1200 may be arranged such that evacuation of the water recycling device 1200 may be performed using gravity. For example, the water recycling device 1200 may be arranged such that no water traps are formed in the different paths of the water recycling device 1200. Further, the water recycling device 1200 may be configured to be installed such that the heating arrangement 1236 is arranged above the water treatment arrangement 1232 with respect to gravity. Similarly, the evacuation path 1234 may be arranged above the R/E path 1220 with respect to gravity. In one example, the circulation pump 1228, and/or another pump arranged in the water recycling device 1200, may provide for a flow of water such that the water recycling device 1200 can be emptied.

Yet another advantage with an arrangement according to the present disclosure is that external water may enter the valve arrangement 1226, flow via the treatment path 1230 to the inlet of the evacuation path 1234, and be directed to the drain 1216 via the return path 1222 and R/E path 1220. Hereby, the water recycling device 1200 may be flushed with external water. For example, the drain 1216 may be flushed by external water. The drain 1216 may for example comprise a pre-filter for filtering water collected from the outlet 1238, such as used water. The pre-filter may be a mesh filter. In this case yet another advantage is that the pre-filter may be flushed by external water. The water recycling device 1200 may comprise a sensor arrangement. The sensor arrangement may be arranged in the drain 1216. The sensor arrangement may be configured to measure a number of water quality parameters in water in the water recycling device and/or in water collected by the drain 1216. The sensor arrangement may be configured to determine a water quality measure of water in the water recycling device. The sensor arrangement may comprise an electrical conductivity sensor and a UV-sensor. The electrical conductivity sensor may be arranged in the drain 1216. The UV-sensor may be arranged in the heating arrangement 1236. In this case yet another advantage is that external water may pass the sensor arrangement when the water recycling device is emptied, and thus external water may be measured by the sensor arrangement in order to set a reference value for the number of water quality parameter.

Yet another advantage with an arrangement according to the present disclosure is that water in at least part of the treatment path 1230, the evacuation path 1234, and return path 1222 may circulate in the treatment path 1230, the evacuation path 1234, and return path 1222. In other words, at least part of the treatment path 1230, the evacuation path 1234, and return path 1222 may form a loop. This water may for example be used water, external water, treated water, or any combination of used, external, and treated water. Hereby, the circulation pump 1228 may be flushed.

Yet another advantage with an arrangement according to the present disclosure is that an internal cleaning and disinfection may be achieved by adding chemicals to the drain 1216 and a disinfection cycle may subsequently be triggered. The disinfection cycle may draw water, containing the chemicals, from the drain 1216 into any of the water treatment arrangement 1232, circulation pump 1228, valve arrangement 1226, and heating arrangement 1236, or any of the R/E path 1220, return path 1222, evacuation path 1234, and treatment path 1230. The disinfection cycle may be triggered from an application on a smart device, such as a smart phone.

The drain 1216 may comprise a drain discard path 1242. The drain discard path 1242 may be separated from the inlet of the R/E path 1220, such that used water which is not intended to be treated by the water treatment arrangement 1232, and thus not intended to be recycled, does not have to enter the inlet of the R/E path 1220 in order to reach the drain discard path 1242. Hereby, contaminated water may be prevented from contaminating any of the elements being arranged downstream of the inlet of the R/E path 1220.

Referring now to FIG. 10, a water recycling device 1300 similar to the water recycling device 1200 described in conjunction with FIG. 9 is illustrated. It is to be understood that the water recycling device 1300 may comprise any of the features described above in conjunction with FIG. 9. The water recycling device 1300 may comprise a first and a second valve arrangement 1326, 1327. The first valve arrangement 1326 may be configured to accept as input the used water from the return path 1322. The first valve arrangement may be configured to direct the used water from the return path 1322 to the treatment path 1330. The second valve arrangement 1327 may accept as input the external water from the external water path 324. The second valve arrangement 1327 may be configured to direct the external water to the treatment path 1330. The second valve arrangement 1327 may be configured to direct the used water received from the first valve arrangement 1326 to the treatment path 1330. The first valve arrangement 1326 may be configured to direct the used water from the return path 1322 to the valve discard path 1340.

Referring now to FIGS. 11-13, flow directions in a water recycling device are illustrated. Referring first to FIG. 11, when outputting water from the water recycling device, used water may be collected by the drain and enter the R/E path via the inlet of the R/E path. The used water may then be directed to the return path, and the valve arrangement. Used water, and only used water, may thus be directed to the water treatment arrangement and output by the outlet of the water recycling device. This may for example be the case if a water quality measure of the used water is above a first quality threshold and a second quality threshold. At the valve arrangement, external water may enter the water recycling device. This may for example be the case if a water quality measure of the used water is above the first quality threshold, but below a second quality threshold. In other words, a combination of used water and external water is used. It is to be understood that it is possible to use only used water, only external water, or a combination of the two. External water, and only external water, may for example be used if a water quality measure of the used water below a first quality threshold. Water to be treated may then enter the treatment path via the circulation pump and be directed to the water treatment arrangement. Treated water may then enter the heating arrangement, and subsequently be output from the outlet.

It is also possible to direct used water to the evacuation path (not shown). In this case, used water in the treatment path is first allowed to leave the treatment path via the evacuation path, the R/E path, and the drain, and optionally via the outlet in case any used water has already passed the inlet of the evacuation path. External water may then enter the valve arrangement and subsequently enter the treatment path and be output from the outlet via the water treatment arrangement. Hereby, it is possible to discharge used water which is for any reason deemed to be inadequate for recycling, for example if a water quality measure of the used water is below a first quality threshold.

Yet another possibility is for used water to enter the drain, and subsequently enter the drain discard pipe. This may for example be the case if the used water is for any reason deemed to be inadequate for recycling, for example if a water quality measure of the used water is below the first quality threshold and the second quality threshold. In this case used water never enters the inlet of the R/E path. Instead, external water may enter the valve arrangement, and subsequently enter the treatment path and be output from the outlet via the water treatment arrangement.

Yet another possibility is to fill the water recycling device with water. For example, external water may be introduced to the water recycling device. This may be achieved by setting the valve arrangement to accept external water as input, the evacuation valve arrangement to prevent a flow of water into the evacuation path, and by the circulation pump providing a flow of water in the water recycling device. External water may be allowed to fill the water recycling device to a level such that external water is introduced into the heating arrangement.

Referring now to FIG. 12, the evacuation valve arrangement may be set to allow a flow of water into the evacuation path, such that the water recycling device may be emptied. The circulation pump may in this case be turned off. Water may thus drain from the treatment path via the heating arrangement, the water treatment arrangement, the evacuation path, and the R/E path to the drain and subsequently to the drain discard pipe. When evacuating the water recycling device, air may be drawn through the outlet in order to equalize a pressure inside the water recycling device. The air drawn through the outlet may assist in keeping the water treatment arrangement dry, thus reducing the possibility of growth of microorganisms in the water treatment arrangement.

Referring now to FIG. 13, used water and/or external water may be looped through the treatment path, the evacuation path, and the return path. This may be achieved by first providing used and/or external water to the water recycling device. Subsequently, the valve arrangement may be set to only accept water received from the return path. The evacuation valve arrangement may be set to allow a flow of water into the evacuation path. The circulation pump may provide a flow for looping water through the treatment path, the evacuation path, and the return path.

Referring now to FIG. 14, a method for evacuating a water recycling device is illustrated in a flow chart diagram. The method comprises the step 1742 of feeding water in the water recycling device to the drain via the evacuation path and/or the return/evacuation path.

A method for evacuating a water recycling device is described below. The water recycling device may comprise an outlet configured to output treated water; a drain for collecting used water output from the outlet; a return/evacuation path in liquid communication with the drain, wherein the return/evacuation path comprises an inlet for receiving water collected by the drain; a return path in liquid communication with the return/evacuation path; a treatment path in liquid communication with the return path and the outlet; an external water path in liquid communication with the treatment path, the external water path being connected to an external water outlet; a valve arrangement, wherein the valve arrangement is configured to accept as inputs used water from the return path and/or external water from the external water path, the valve arrangement being placed between the return path and the treatment path, the valve arrangement being configured to direct the inputs to the treatment path, the valve arrangement being configured to mix the external water with the used water from the return path; a circulation pump for providing a flow in the water recycling device; a water treatment arrangement placed downstream of the valve arrangement; and an evacuation path in liquid communication with the treatment path, wherein the evacuation path is placed downstream of the circulation pump and upstream of the water treatment arrangement. The method may comprise the steps of feeding water in the water recycling device to the drain via the evacuation path and/or the return/evacuation path. The step of feeding water in the water recycling device to the drain via the evacuation path and/or the return/evacuation path may be accomplished by gravity.

A method for cleaning a water recycling device is described below. The water recycle device may comprise an outlet configured to output treated water; a drain for collecting used the water output from the outlet; a return/evacuation path in liquid communication with the drain, wherein the return/evacuation path comprises an inlet for receiving water collected by the drain; a return path in liquid communication with the return/evacuation path; a treatment path in liquid communication with the return path and the outlet; an external water path in liquid communication with the treatment path, the external water path being connected to an external water outlet; a valve arrangement, wherein the valve arrangement is configured to accept as inputs used water from the return path and/or external water from the external water path, the valve arrangement being placed between the return path and the treatment path, the valve arrangement being configured to direct the inputs to the treatment path, the valve arrangement being configured to mix the external water with the used water from the return path; a circulation pump for providing a flow in the water recycling device; a water treatment arrangement placed downstream of the valve arrangement; and an evacuation path in liquid communication with the treatment path, wherein the evacuation path is placed downstream of the circulation pump and upstream of the water treatment arrangement. The method may comprise the steps of providing the water recycling device with the used water, the external water, or a combination of the used water and the external water; and evacuating the water recycling device according to the method for evacuating a water recycling device as described above.

The step of providing the water recycling device with the used water, the external water, or a combination of the used water and the external water may comprise a sub-step of at least partly filling the water treatment arrangement with the used water, the external water, or the combination of the used water and the external water.

The step of providing the water recycling device with the used water, the external water, or the combination of the used water and the external water may comprise a sub-step of circulating the used water, the external water, or the combination of the used water and the external water in the evacuation path, the return path, and at least part of the treatment path.

The water recycling device may further comprise a heater arrangement placed downstream of the water treatment arrangement and/or combined with the water treatment arrangement, and the step of providing the water recycling device with the used water, the external water, or the combination of the used water and the external water may comprise a sub-step of heating the used water, the external water, or the combination of the used water and the external water in the heating arrangement.

The inventive concept has mainly been described above with reference to a few embodiments. However, as is readily appreciated by a person skilled in the art, other embodiments than the ones disclosed above are equally possible within the scope of the inventive concept, as defined by the appended patent claims.

LIST OF REFERENCE SIGNS

1100 Recirculation loop
1102 Nozzle
1104 Drain
1106 Valve
1107 Valve
1108 Discard water pipe
1110 Pump
1112 Potable water source
1200 Water recycling device
1216 Drain
1218 Inlet
1220 Return/Evacuation path
1222 Return path
1224 External water path
1226 Valve arrangement
1228 Circulation pump
1230 Treatment path
1232 Water treatment arrangement
1234 Evacuation path
1236 Heating arrangement
1238 Outlet
1240 Valve discard path
1242 Drain discard path
1300 Water recycling device
1322 Return path
1324 External water path
1326 First valve arrangement
1327 Second valve arrangement
1330 Treatment path
1340 Valve discard path 1742 Step of feeding water to drain via evacuation path and/or return/evacuation path

CLAUSES

1. A water recycling device comprising:
an outlet configured to output treated water;
a drain for collecting used water output from said outlet;
a return/evacuation path in liquid communication with said drain, wherein said return/evacuation path comprises an inlet for receiving water collected by said drain;
a return path in liquid communication with said return/evacuation path;
a treatment path in liquid communication with said return path and said outlet;
an external water path in liquid communication with said treatment path, said external water path being connected to an external water outlet;
a valve arrangement configured to accept as inputs used water from said return path and/or external water from said external water path, said valve arrangement being placed between said return path and said treatment path, said valve arrangement being configured to direct said inputs to said treatment path, said valve arrangement being configured to mix said external water with said used water from said return path;
a circulation pump for providing a flow in said water recycling device; and
a water treatment arrangement placed downstream of said valve arrangement.

2. The water recycling device according to any one of the preceding clauses, further comprising a heating arrangement placed downstream of said water treatment arrangement.

3. The water recycling device according to clause 1 or 2, further comprising an evacuation path in liquid communication with said treatment path, wherein said evacuation path is placed downstream of said valve arrangement and upstream of said water treatment arrangement.

4. The water recycling device according to clause 3, wherein said water recycling device is configured to circulate water in at least part of said treatment path, said evacuation path, and said return path.

5. The water recycling device according to any one of the preceding clauses, wherein said return/evacuation path is configured to be in a first state, wherein water in said return/evacuation path is allowed to flow in a direction away from said drain, and a second state, wherein water in said return/evacuation path is allowed to flow in a direction towards said drain.

6. A water recirculating shower comprising a water recycling device according to any one of clauses 1 to 5.

7. A method for evacuating a water recycling device, said water recycling device comprising:
an outlet configured to output treated water;
a drain for collecting used water output from said outlet;
a return/evacuation path in liquid communication with said drain, wherein said return/evacuation path comprises an inlet for receiving water collected by said drain;
a return path in liquid communication with said return/evacuation path;
a treatment path in liquid communication with said return path and said outlet;
an external water path in liquid communication with said treatment path, said external water path being connected to an external water outlet;

a valve arrangement, wherein said valve arrangement is configured to accept as inputs used water from said return path and/or external water from said external water path, said valve arrangement being placed between said return path and said treatment path, said valve arrangement being configured to direct said inputs to said treatment path, said valve arrangement being configured to mix said external water with said used water from said return path;

a circulation pump for providing a flow in said water recycling device;

a water treatment arrangement placed downstream of said valve arrangement; and an evacuation path in liquid communication with said treatment path, wherein said evacuation path is placed downstream of said circulation pump and upstream of said water treatment arrangement;

wherein said method comprises the steps of:

feeding water in said water recycling device to said drain via said evacuation path and/or said return/evacuation path.

8. The method according to clause 7, wherein said step of feeding water in said water recycling device to said drain via said evacuation path and/or said return/evacuation path is accomplished by gravity.

9. A method for cleaning a water recycling device, said water recycling device comprising:

an outlet configured to output treated water;

a drain for collecting used said water output from said outlet;

a return/evacuation path in liquid communication with said drain, wherein said return/evacuation path comprises an inlet for receiving water collected by said drain;

a return path in liquid communication with said return/evacuation path;

a treatment path in liquid communication with said return path and said outlet;

an external water path in liquid communication with said treatment path, said external water path being connected to an external water outlet;

a valve arrangement, wherein said valve arrangement is configured to accept as inputs used water from said return path and/or external water from said external water path, said valve arrangement being placed between said return path and said treatment path, said valve arrangement being configured to direct said inputs to said treatment path, said valve arrangement being configured to mix said external water with said used water from said return path;

a circulation pump for providing a flow in said water recycling device;

a water treatment arrangement placed downstream of said valve arrangement; and an evacuation path in liquid communication with said treatment path, wherein said evacuation path is placed downstream of said circulation pump and upstream of said water treatment arrangement;

said method comprising the steps of:

providing said water recycling device with said used water, said external water, or a combination of said used water and said external water; and evacuating said water recycling device according to the method of clause 7 or 8.

10. The method for cleaning a water recycling device according to clause 9, wherein said step of providing said water recycling device with said used water, said external water, or said combination of said used water and said external water comprises a sub-step of at least partly filling said water treatment arrangement with said used water, said external water, or a combination of said used water and said external water.

11. The method for cleaning a water recycling device according to clause 9 or 10, wherein said step of providing said water recycling device with said used water, said external water, or said combination of said used water and said external water comprises a sub-step of circulating said used water, said external water, or said combination of said used water and said external water in said evacuation path, said return path, and at least part of said treatment path.

12. The method for cleaning a water recycling device according to any one of clauses 9 to 11, wherein said water recycling device further comprises a heater arrangement placed downstream of said water treatment arrangement and/or combined with said water treatment arrangement, wherein said step of providing said water recycling device with said used water, said external water, or said combination of said used water and said external water comprises a sub-step of heating said used water, said external water, or said combination of said used water and said external water in said heating arrangement.

The invention claimed is:

1. A method for recycling water in a water recycling device, said method comprising:

receiving used water via a drain;

determining a water quality measure of said used water;

if said water quality measure of said used water is above a first quality threshold, feeding said used water to a valve arrangement;

in said valve arrangement, forming water to be treated by providing external water, said used water or a combination of said external water and said used water;

generating treated water by treating said water to be treated using a water treatment arrangement; and feeding said treated water to an outlet.

2. The method according to claim 1, wherein said step of forming water to be treated by providing external water, said used water or a combination of said external water and said used water, wherein only said external water is provided for forming said water to be treated if said water quality measure is below said first quality threshold.

3. The method according to claim 2, wherein said step of forming water to be treated by providing external water, said used water or a combination of said external water and said used water, wherein only said external water is provided for forming said water to be treated if said water quality measure is below said first quality threshold and a second quality threshold.

4. The method according to claim 1, wherein said step of generating treated water by treating said water to be treated using a water treatment arrangement comprises sub-steps of filtering said water to be treated, and reducing a harmful effect of microorganisms in said water to be treated by using UV light.

5. A water recycling device comprising:

an outlet configured to output treated water;

a drain for collecting used water output from said outlet;

a sensor configured for determining a water quality measure of the used water;

a return path in liquid communication with said drain;

a treatment path in liquid communication with said return path and said outlet;

an external water path in liquid communication with said treatment path, said external water path being connected to an external water outlet;

a valve arrangement configured to accept as inputs said used water from said return path and/or external water from said external water path, said valve arrangement being placed between said return path and said treatment path, said valve arrangement being configured to direct said inputs to said treatment path, said valve arrangement being configured to mix said external water with said water from said return path;

a circulation pump for providing a flow in said water recycling device; and a water treatment arrangement placed downstream of said valve arrangement.

6. The water recycling device according to claim 5, further comprising a heating arrangement placed downstream of and/or combined with said water treatment arrangement, wherein said heating arrangement is combined with a UV light treatment arrangement into a single piece of equipment.

7. The water recycling device according to claim 5, wherein said water treatment arrangement comprises a filter arrangement.

8. The water recycling device according to claim 5, further comprising a valve discard path configured to discharge water from said water recycling device, wherein said valve arrangement is further configured to direct said water from said return path to said valve discard path.

9. The water recycling device according to claim 5, wherein said valve arrangement comprises at least a first and a second valve arrangement, wherein said first valve arrangement is configured to accept as input said used water from said return path, said first valve arrangement being configured to direct said used water from said return path to said treatment path, and wherein said second valve arrangement accepts as input said external water from said external water path, said second valve arrangement being configured to direct said external water to said treatment path.

10. The water recycling device according to claim 5, wherein said drain comprises a drain discard path configured to discharge used water from said water recycling device.

11. A water recirculating shower comprising a water recycling device according to claim 5.

12. The method according to claim 1, wherein said step of forming water to be treated by providing external water, said used water or a combination of said external water and said used water, wherein only said used water is provided for forming said water to be treated if said water quality measure is above said first quality threshold.

13. The method according to claim 3 wherein said step of forming water to be treated by providing external water, said used water or a combination of said external water and said used water, wherein providing said combination of said external water and said used water for forming said water to be treated if said water quality measure is above said first quality threshold but below said second quality threshold.

14. The method according to claim 3, wherein said step of forming water to be treated by providing external water, said used water or a combination of said external water and said used water, wherein only said used water is provided for forming said water to be treated if said water quality measure is above said first quality threshold and said second quality threshold.

\* \* \* \* \*